United States Patent [19]

Saitoh et al.

[11] Patent Number: 4,692,799
[45] Date of Patent: Sep. 8, 1987

[54] AUTOMATIC INSPECTION SYSTEM FOR DETECTING FOREIGN MATTER

[75] Inventors: Michihiro Saitoh; Takatoshi Gogami; Toshiyuki Osada, all of Kanagawa, Japan

[73] Assignee: Showa Electric Wire & Cable Co., Ltd., Japan

[21] Appl. No.: 943,813

[22] Filed: Dec. 29, 1986

Related U.S. Application Data

[63] Continuation of Ser. No. 819,471, Jan. 15, 1986, abandoned, which is a continuation of Ser. No. 537,114, Sep. 20, 1983, abandoned, which is a continuation-in-part of Ser. No. 374,904, May 4, 1982, abandoned.

[30] Foreign Application Priority Data

Apr. 5, 1982 [JP] Japan .................................. 57/56467
Sep. 2, 1983 [JP] Japan ................................ 58/162395

[51] Int. Cl.$^4$ .............................................. H04N 7/18
[52] U.S. Cl. ..................................... 358/106; 226/45; 250/562
[58] Field of Search ................ 242/75.52, 75.51, 75.53; 226/45; 425/135, 140, 141, 164, 376 R; 358/101, 106; 250/561, 562, 563; 356/237, 238, 430, 431; 264/40.1, 40.7

[56] References Cited

U.S. PATENT DOCUMENTS

| | | | |
|---|---|---|---|
| 2,877,397 | 3/1959 | Poschner et al. | 226/45 |
| 2,897,370 | 7/1959 | Sauter | 226/45 |
| 2,935,559 | 5/1960 | Dornier | 178/6.8 |
| 3,277,305 | 10/1966 | Anderman, Jr. | 276/45 |
| 3,448,279 | 6/1969 | Lindemann et al. | 250/562 |
| 3,560,096 | 2/1971 | Watson et al. | 356/156 |
| 3,940,042 | 2/1976 | Keck | 226/45 |
| 3,988,530 | 10/1976 | Ikegami et al. | 178/6 |
| 4,110,048 | 8/1978 | Akutsu et al. | 356/200 |
| 4,124,340 | 11/1978 | La Spisa et al. | 425/135 |
| 4,319,270 | 3/1982 | Kimura et al. | 358/106 |

FOREIGN PATENT DOCUMENTS 2932660 2/1981 Fed. Rep. of Germany ...... 356/237

*Primary Examiner*—Joseph A. Orsino, Jr.
*Attorney, Agent, or Firm*—Pahl, Lorusso & Loud

[57] ABSTRACT

An automatic inspection system detects foreign materials included in a sheet of transparent or translucent resin material such as a polyethylene compound. The automatic inspection system comprises an extruder for extruding a resin material into a sheet, means for withdrawing the extruded sheet along a path of travel, means disposed between the extruder and the withdrawing means for permitting the sheet to having down by gravity into a U-shape, sensor means for detecting a vertical position of the U-shaped portion of the sheet, controller means for adjusting the speed of sheet withdrawal for the withdrawing means in response to the output signal from the sensor means, a source of light disposed on one side of the path of travel of the sheet, an image sensor camera disposed on the other side of the path of travel of the sheet in confronting relation to the source of light for receiving light emitted from the source of light and having passed through the sheet to detect foreign materials included in the sheet.

3 Claims, 8 Drawing Figures

4,692,799

AUTOMATIC INSPECTION SYSTEM FOR DETECTING FOREIGN MATTER

BACKGROUND OF THE INVENTION

This is a continuation of Ser. No. 819,471, filed Jan. 15, 1986, now abandoned, which is a continuation of Ser. No. 537,114, filed Sept. 29, 1983, now abandoned, which is a continuation-in-part of our application Ser. No. 374,904 filed May 4, 1982 now abandoned for Automatic Inspection System for Detecting Foreign Matter.

The present invention relates to an automatic inspection system for detecting foreign matter or material such as dirt or metal particles included in a translucent or transparent resin material such as a polyethylene compound used as a sheath for an electrical wire or cable.

Translucent or transparent resin materials such as polyethylene compounds used as sheaths for electrical wires or cables are inspected for foreign material trapped therein. According to one known inspection system for detecting such foreign material in the compound, the compound is extruded into a sheet which is visually checked for foreign material with a magnifying glass having a magnifying power of about ten, an area on the sheet which appears to include foreign matter is marked in red, and the marked area is once again visually inspected with a microscope which is about 100-power to determine the sizes, number and kind of foreign materials or particles included. With the known inspection system, resin materials having included therein foreign material having a size of 100 microns or less are classified as "grade A," and those including foreign material having a size in the range of from 100 microns to 200 microns as "grade B" for the purpose of guiding the user as to the best applications for the resin materials.

The prior inspection process, however, takes one and half hours for inspecting a sheet that is 2 m long, suffers from errors because of sole reliance on the inspector's visual inspection, and is mentally and physically fatiguing to the inspector, rendering it difficult to carry out continuous inspection operation.

There is also known a fault type detector for surface scanning, comprising a signal generator, trippering flash illuminating faulty surface section for recording (DE-OS No. 2932660).

This detector, however, has a shortcoming that it can not automatically detect the web or strip immediately after it is extruded.

SUMMARY OF THE INVENTION

The above-described drawbacks in the prior art apparatus have been successfully eliminated by the present invention.

Accordingly, it is an object of the present invention to provide an automatic inspection system capable of continuously detecting foreign material in a resin material sheet immediately after it is extruded.

Another object of the present invention is to provide an automatic inspection system capable of statistically processing detected foreign materials for information as to the number, sizes, kind and the like of the foreign materials.

According to the present invention, the above objects can be achieved by an automatic inspection system for detecting foreign material in a resin sheet comprising an extruder for extruding a resin material into the sheet, means for withdrawing the extruded sheet along a path of travel, means disposed between said extruder and the withdrawing means for permitting the sheet to having down by gravity into a U-shape; sensor means for detecting a vertical position of the U-shaped portion of the sheet; controller means for adjusting the speed of sheet withdrawal for the withdrawing means in response to the output signal from the sensor means; a source of light disposed on one side of the path of travel of the sheet; and an image sensor camera disposed on the other side of the path of travel of the sheet in confronting relation to the source of light for receiving light emitted from the source of light and having passed through the sheet to detect foregin material included in the sheet.

With the automatic inspection system of the invention, the kinds, the sizes, the number and other statistical information of the detected foreign materials are available to a nicety for quick determination of acceptance or nonacceptance of a resin material being inspected and the grade thereof. The time required for such processing can greatly be reduced as compared prior art with manual or machinery inspection, and hence the inspection process can be simplified.

These and other objects of the invention will become apparent from the following description of an embodiment thereof when taken together with the drawings.

DETAILED DESCRIPTION OF THE PREFERRED EMBODIMENT

Figure 1:
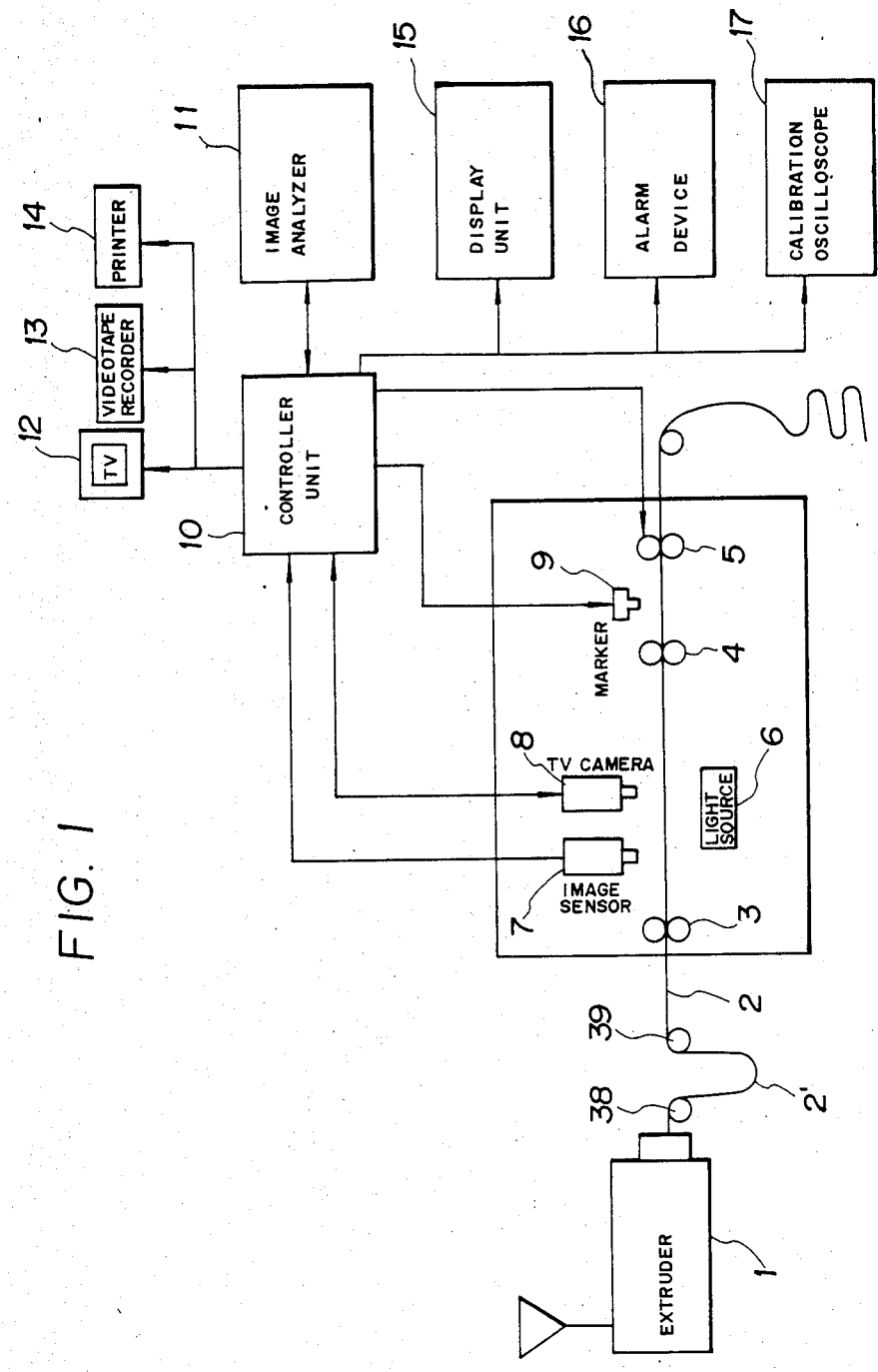
FIG. 1 is a schematic diagram of an automatic inspection system for detecting foreign material according to an embodiment of the present invention.
Figure 2:
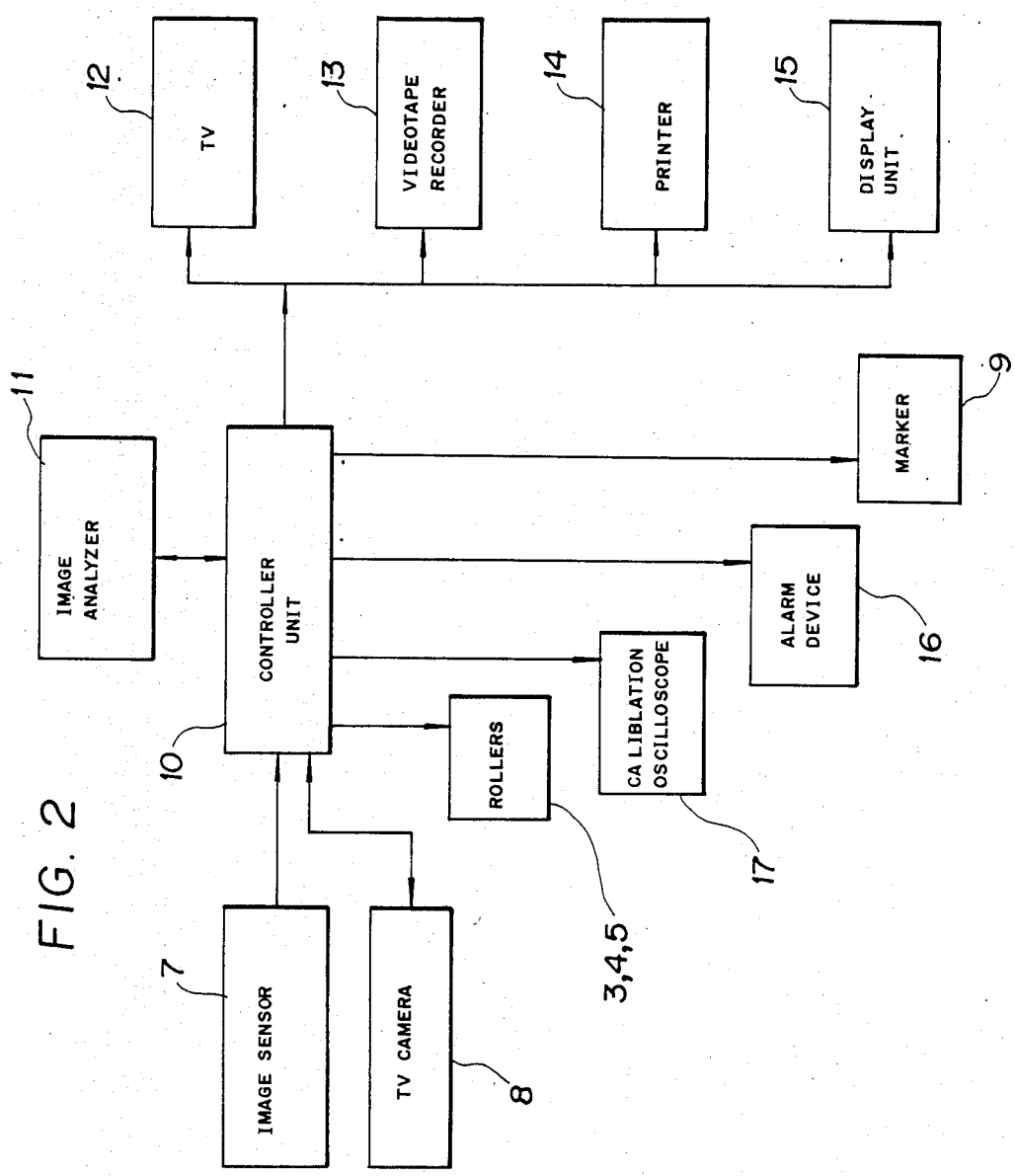
FIG. 2 is a block diagram of the automatic inspection system shown in FIG. 1.

FIGS. 1 and 2 show an automatic inspection system according to the present invention, the system being illustrated partly in block form in FIG. 1 and fully in block form in FIG. 2.

As shown in FIG. 1, a compound such as of polyethylene is extruded by a small-type extruder 1 into a sheet 2 of a width of 50 mm and a thickness of 1 mm, for example. The sheet 2 is withdrawn by rollers 3, 4 and 5 and guided thereby to travel along a rectilinear path.

Automatization of the apparatus requires that the sheet 2 extruded at a given speed from the extruder 1 be withdrawn at a constant speed by the rollers 3, 4, 5. Since the sheet 2 immediately after it is extruded is likely to rupture as the resin remains still soft, the sheet should be withdrawn after it has been cooled and hardened or cured sufficiently to allow its safe withdrawal. One proposal would be to provide a water-cooled cooling unit following the extruder 1. However, such a cooling unit could not be installed in applications in which no sufficient space is available therefor, and would be disadvantageous in that it would prevent the monitoring of extrusion of the sheet 2.

Figure 6:
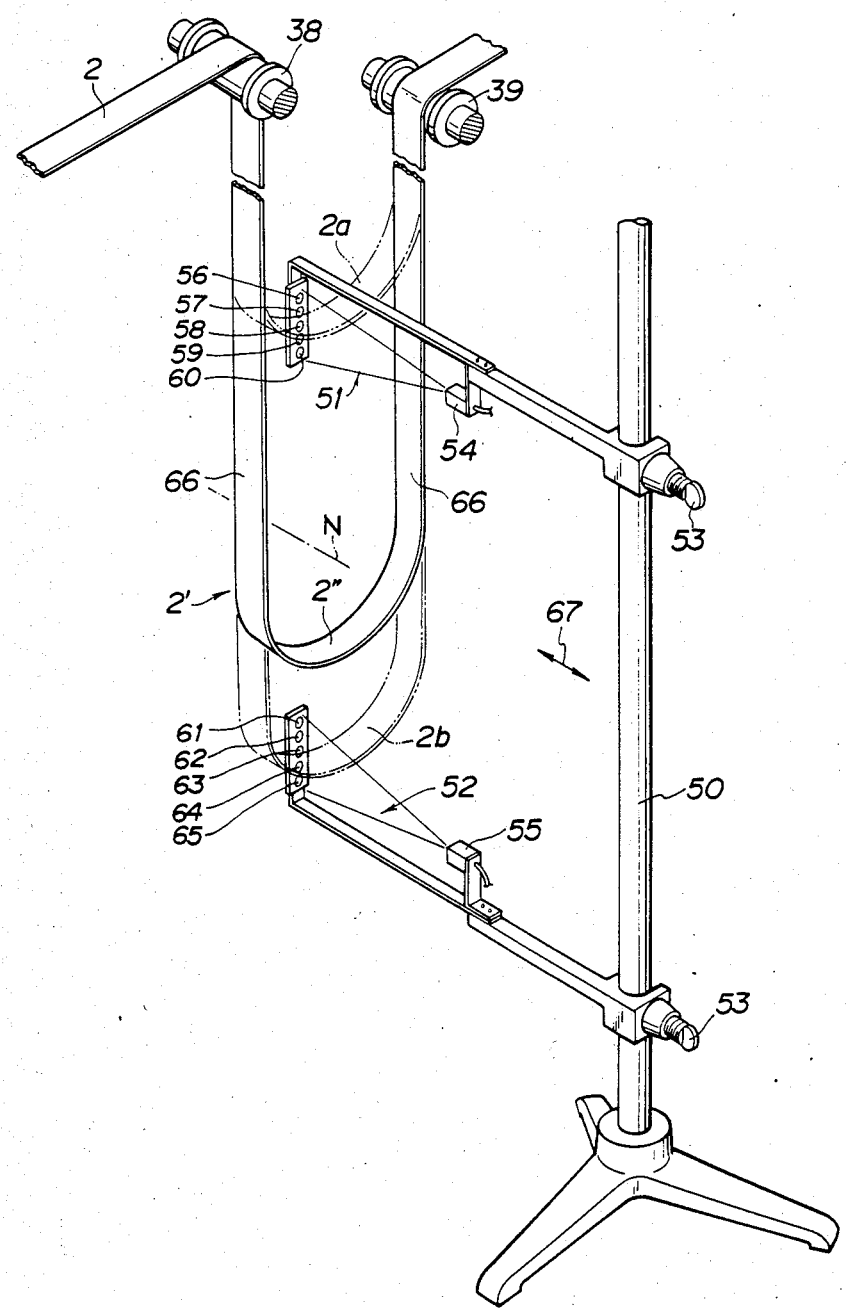
FIG. 6 is a perspective view of a U-shaped portion of the sheet disposed between the extruder and withdrawing rollers, and coupled sensors for detecting a vertical position of the U-shaped portion.

With the system of the present invention, rollers 38, 39 are disposed between the extruder 1 and the withdrawal rollers 3, 4, 5, as shown in FIG. 1, for permitting the sheet 2 to hang down by gravity into a U-shaped portion 2'. FIG. 6 illustrates in detail the rollers 38, 39 and the manner in which the sheet 2 hangs down therebetween. While the sheet 2 is hanging down by gravity and travelling along the U-shaped path for an increased period of time, the sheet 2 can sufficiently be cooled and hardened by ambient air to the extent where it can safely be withdrawn by the withdrawal rollers 3, 4, 5.

Figure 5:
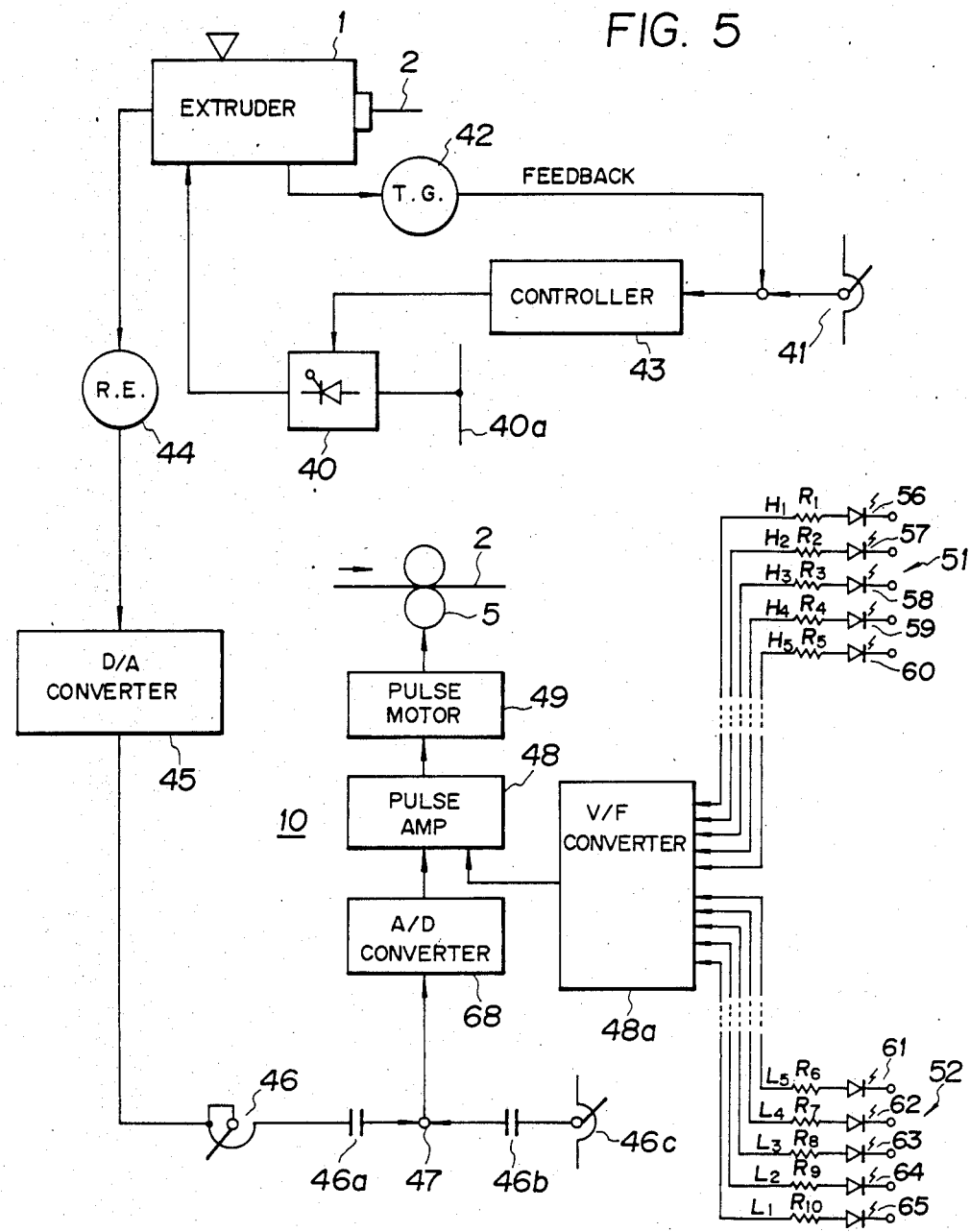
FIG. 5 is a diagram illustrative of a system for controlling the speed of sheet withdrawal.

With the sheet 2 hanging down in the shape of a U, the speed of withdrawal of the sheet 2 can easily be controlled in the following manner:

The extruder 1 has a screw (not shown) rotated by a variable-speed motor energized by a power supply unit 40 phase-controlled by a thyristor stack, for example, as illustrated in FIG. 5. The power supply unit 40 is powered by an a.c. power supply line 40a. The rate of extrusion is finely adjusted by a regulator 41 as it varies with the resin material used and season (ambient air temperature). An output from the regulator 41 is applied to a controller 43 which controls the phase of the thyristor stack in the power supply unit 40.

Rotation of the motor or screw in the extruder 1 is detected by a tachogenerator 42 and applied as a feedback signal to the controller 43, thus providing an automatic control system for keeping the rate of extrusion by the extruder 1 constant.

A system for controlling the speed of sheet withdrawal will be described.

To bring the speed of withdrawal by the withdrawal rollers 3, 4, 5 into synchronism with the constant rate of extrusion by the extruder 1 as controlled above, rotation of the extruder screw 2 is detected by a rotary encoder 44, and a detected signal is converted into an analog signal by a D/A converter 45. The analog signal is then applied through a regulator 46 and a changeover switch 46a to an adder point 47. A signal from a manual regulator 46c is fed through a changeover switch 46b to the adder point 47. A signal from the adder point 47 is converted by an A/D converter 68 into a digital signal, which is amplified by a pulse amplifier 48. The amplified signal is applied to a pulse motor 49 which drives the withdrawal rollers 5. For automatically synchronizing the withdrawal speed with the extrusion rate, the switch 46a is turned on and the switch 46b is turned off. For manual speed adjustment, the switch 46a is turned off and the switch 46b is turned on, and the manual regulator 46c is manually controlled to drive the rollers 5. The foregoing arrangement constitutes a main synchronous control system by which the speed of withdrawal by the rollers 3, 4, 5 can be brought into synchronism with the rate of extrusion by the extruder 1, and the sheet 2 can travel with the U-shaped hanging portion 2' having a desired length. However, the bottom 2" of the U-shaped sheet portion 2' tends to vary up and down in position due to a difference between the extrusion speed and the withdrawal speed for a variety of reasons. A corrective control system for compensating for such a speed difference will now be described.

As shown in FIG. 6, sensors 51, 52 are mounted on a post 50 in vertically spaced relation for detecting the vertical position of the U-shaped portion of the sheet 2, the sensors 51, 52 being vertically positionally adjustable by screws 53. The sensors 51, 52 comprise light-emitting elements 54, 55 such as halogen lamps and photodetector elements 56-60, 61-65 such as photodiodes. Light rays emitted from the light-emitting elements 54, 55 travel toward the photodetector elements 56-60, 61-65, respectively, along optical axes extending substantially parallel to the axis around which the U-shaped portion 2' of the sheet 2 extends. The optical axes therefore extend parallel to a surface 66 of the U-shaped portion 2'. The bottom 2" of the U-shaped portion 2' is initially positioned intermediate between the sensors 51, 52. The post 50 is moved in the directions of the arrow 67 so that the U-shaped portion 2' will be positioned between the light-emitting element 54 and the photodetector elements 56-60 and the light-emitting element 55 and the photodetector elements 61-65. In operation, the photodetector elements 56-60, 61-65 produce d.c. signals H1-H5, L1-L5 (FIG. 5), respectively, through level adjusters R1-R5, R6-R10, respectively. The voltage outputs are then applied to a voltage-to-frequency converter 48a. A frequency (pulse) output from the voltage-to-frequency converter 48a is then applied to the pulse amplifier 48. More specifically, the sensor 51 produces the d.c. signals H1-H5 which are varied in level by the level adjusters R1-R5 so that the signals have the relationship: $H1 > H2 > H3 > H4 > H5$, these signals serving to lower the speed of withdrawal of the sheet. The sensor 52 produces the d.c. signals L1-L5 which are varied in level by the level adjusters R6-R10 so that the signals have the relationship: $L1 > L2 > L3 > L4 > L5$, these signals serving to increase the speed of sheet withdrawal. The number of photodetector elements in each sensor is not limited to five, and the level adjusters may comprise other devices such as transistors. The above corrective control system is incorporated in a controller unit 10 (FIGS. 1 and 2) which will be described later on.

The corrective control system will operate as follows: It is now assumed that the U-shaped portion 2' of the sheet 2 hangs down of its own accord by gravity with its bottom 2" positioned intermediate between the sensors 51, 52 as indicated by the solid line in FIG. 6, i.e., in a neutral position N (FIG. 6), and the sheet 2 is cooled as it is withdrawn by the rollers 3, 4, 5. In this condition, the rollers 5 are driven by the main synchronous automatic control system composed of the rotary encoder 44, the D/A converter 45, the regulator 46, the A/D converter 68, the pulse amplifier 48, and the pulse motor 49. When the U-shaped sheet portion 2' is moved upwardly, for some reasons, from the neutral position up to a position (indicated by 2a in FIG. 6) in which the sheet blocks light toward the photodetector element 60, the latter produces a correction signal H5 for increasing the speed of sheet withdrawal. The correction signal H5 is then converted by the converter 48a into a corresponding frequency (pulse), which is applied to the pulse amplifier 48 as pulses for reducing the number of pulses in the main synchronous control system. As the U-shaped portion 2' goes progressively upwardly, the sensor 51 successively produces the signals H4, H3, H2, H1 ($H4 > H3 > H2 > H1$) to reduce the speed of sheet withdrawal. Conversely, when the U-shaped portion 2' is lowered from the neutral position down to a position (shown at 2b in FIG. 6) in which it blocks light toward the photodetector element 61, which then produces a correction signal L5 for speeding up the sheet withdrawal. The correction signal L5 is converted into pulses that will be added to the pulses generated in the main synchronous control system. Progressing downward movement of the U-shaped portion 2' causes the sensor 52 to successively generate the signals L4, L3, L2, L1 (L4<L3<L2<L1) to increase the speed of sheet withdrawal. Accordingly, when the U-shaped portion 2' is vertically displaced from the neutral position, the sensor 31 or 32 detects its vertical position through five steps and produces an output signal for controlling the pulse motor 49 to enable the rollers 5 to adjust the speed at which the sheet 2 is withdrawn. Thus, the U-shaped sheet portion 2' hanging down between the rollers 38, 39 is advantageous in that it can cool the sheet 2 sufficiently to be safely withdrawn by the rollers, and also can adjust the speed of sheet withdrawal into synchronism with the speed of sheet extrusion.

An inspection system for detecting foreign matter according to the present invention will now be descirbed. A source 6 of light is disposed downwardly of the sheet 2 and between the rollers 3 and 4, and an image sensor camera (hereinafter referred to as an "image sensor") 7 and a television camera 8 are disposed upwardly of the sheet 2 and between the rollers 3 and 4 in confronting relation to the light source 6. A marker or a blanking punch 9 is located between the rollers 4 and 5 in overlying relation to the sheet 2 as it moves along the path of travel thereof. The image sensor 7 and the television camera 8 produce outputs which are supplied to a controller unit 10. The controller unit 10 is connected to an image analyzer 11 for measuring the sizes, the number and other data of foreign materials detected, a 9-inch monochrome monitor televison picture tube 12 which is energizable upon detection of foreign materials, a videotape recorder 13 for recording the images of foreign materials as detected by the television camera 8, a printer 14 for printing results of analysis of the foreign materials, a display unit 15 for displaying the results of analysis of the foreign materials, an alarm device 16 that is actuatable when foreign materials are detected, and a calibration oscilloscope 17 for checking the conditions of output signals supplied from the image sensor 7.

The light source 6 may comprise, for example, a halogen lamp (such as 7023 manufactured by Philips) for emitting light having a wavelength of 530 Å. The image sensor 7 is receptive of light emitted from the light source 6 and having passed through the sheet 2. Foreign materials included in the sheet 2 can be detected when the intensity of light reaching the image sensor 7 is reduced by the foreign materials having a lower transmission coefficient. The foreign materials included in the sheet 2 are in the form of metal particles such as of aluminum or copper, fully scorched black materials, less scorched amber materials, and fiberous materials. It is particularly important to detect metal particles trapped in the sheet 2 as they could cause a dielectric breakdown of a cable sheath which is constructed of the sheet 2. The foreign materials that are normally included in the resin material of the type described are relatively small in size, the particle size being in the range of from 100 microns to 200 microns. For an increased accuracy of detection capable of detecting a particle size down to about 25 microns, the image sensor 7 comprises 512 photodiodes each having a square photosensitive surface with a side 28 microns long. Such an image sensor is manufactured by Matsushita Denshi Kogyo K.K. as the model MEL512K. For inspection of a sheet 2 having a width of 5 cm, four such image sensors are arranged in an array across the sheet 2.

Figure 4A:
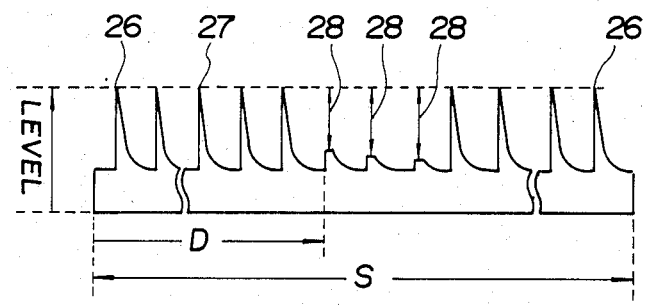
FIG. 4(a) and (b) are the diagram illustrative of the manner in which a foreign material is detected and classified by pulse waveform produced from a corresponding sheet surfaces by scanning.
Figure 4B:
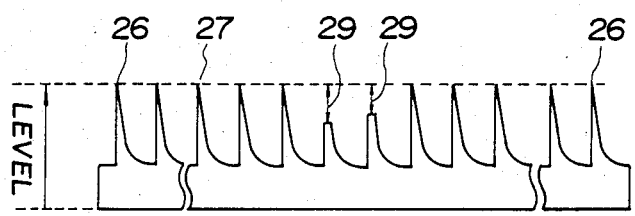

As shown in FIGS. 4(a) and (b), the image sensor 7 scans the photosensitive surfaces continously for producing successive pulse outputs 26. Each pulse 27 of the successive pulse outputs 26 is produced by emitting of the electric charge which cumulated in proportion to the quantity of light received in the corresponding photosensitive surfaces by scanning. A foreign material causes to decrease the output level of the pulse 27 from the corresponding photosensitive surfaces. Therefore foreign material can be detected as a pulse-free portion 28 or a pulse-partially-free portion 29 of pulse-waveform, and the position D of the foreign material transverse S of the sheet 2 can also be determined from the same pulse-wave-form. In case of metal particle, that pulse 27 from the corresponding photosensitive surface produces substantially no pulse. A foreign material is so detected and classified as a metallic or non-metallic material. The size of the foreign material can be measured by processing the pulse-free portion or the pulse-partially-free portion of the pulse waveform with an area analyzer. The number of detected foreign materials is usually on the order of 3 for an interval of 10 m in the longitudianl direction of the sheet 2. The number of foreign materials can be measured by a particle counter. Therefore, the sizes, transverse positions, the kind of metallic or non-metallic, and the number of foreign materials can be detected by suitably processing an output signal delivered from the image sensor 7. According to the illustrated embodiment, however, the output signal from the image sensor 7 is used to compute the transverse positions of the foreign materials in the controller unit 10. The sizes and number of foreign materials are measured by imaging the foreign materials with the television camera 8, which may comprise a television camera manufactured by Hitachi Electronics Co., Ltd., and analyzing the obtained image with the image analyzer 11. To enable the television camera 8 to image foreign materials, a signal which corresponds to the transverse positions of the foreign materials is supplied from the controller unit 10 to the television camera 8 to move the latter transversely of the sheet 2 to the position in which the foreign materials can pass through the field of view of the television camera 8.

Where there are a plurality of foreign materials scattered transversely of the sheet 2, the distances between the foreign materials are derived by the controller unit 10 from the transverse positions of the foreign materials. Then, the controller unit 10 supplies such a signal to the television camera 8 that the camera 8 will be moved longitudinally, with the speed of travel of the sheet 2 taken into consideration, to image a first foreign material and then to follow and image a next foreign material. At the same time, the controller unit 10 generates an alarm signal indicative of the detection of the foreign materials for thereby readying the monitor television picture tube 12 and the videotape recorder 13, and simultaneously for energizing the alarm device 16 to give off a buzzer sound and light an alarm lamp.

The television camera 8 images foreign materials and delivers an image signal to the image analyzer 11 for analyzing the sizes and other data of the foreign materials. The television camera 8 is movable transversely fully across the sheet 2 from edge to edge. The television camera 8 is also movable longitudinally of the sheet 2 for a relatively small interval to the extent that the television camera 8 can follow and image transversely scattered foreign materials, if any, as the sheet continues to move longitudinally. Longitudinally scattered foreign materials can be imaged by moving and readying the television cameras 8 repeatedly transversely of the sheet 2 in advance. Since sheets 2 which are normally presented for inspection are not so long, the field of view of the television camera 8 may be imaged at all times. If necessary, the television camera 8 may start imaging the sheet 2 just before foreign materials reach the field of view of the camera 8 in the same manner as that in which the timing of marking by the marker 9 is determined as will be described later on. The image signal indicative of foreign materials is supplied to the monitor television picture tube 12 and the videotape recorder 13 as well as to the image analyzer 11.

The marker 9 serves to mark an area on the sheet 2 in which foreign materials are present. The marker 9 is responsive to an output from the image sensor 7 to move transversely of the sheet 2 to a position in which foreign materials will come to underlie the marker 9. The timing of marking may be determined by starting to cause the controller unit 10 to count output pulses from a rotary encoder (not shown) connected to the roller 3 when foreign materials are detected, and continuing the counting for an interval during which the sheet 2 travels by the known distance between the image sensor 7 and the marker 9. The marked area of the sheet 2 may subsequently be cut off to allow analysis of foreign materials in a way different from that in which the image analyzer 11 analizes the foreign materials. The marker 9 may be replaced with a blanking punch for blanking an area containing foreign materials off the sheet 2 for immediate analysis of the foreign materials, an arrangement which assists the image analyzer 11 in analyzing the foreign materials.

The monitor television picture tube 12 and the videotape recorder 13 serve to monitor and record, respectively, the image of foreign materials which is picked up by the television camera 8. The monitor television picture tube 12 and the videotape recorder 13 are readied by an alarm signal generated by the controller unit 10 when the image sensor 7 detects foreign materials, and are energized when supplied with an image signal from the television camera 8. The timing of starting of the monitor television picture tube 12 and the videotape recorder 13 can be determined in the same manner as that in which the timing of marking by the marker 9 is determined. The alarm device 16 is responsive to the alarm signal fed from the controller unit 10 for producing a buzzer sound and energizing an alarm lamp. When thus alarmed by the alarm device 16, the operator can immediately watch the foreign materials as displayed on the monitor television picture tube 12.

As described above, the controller unit 10 serves to classify the kind and compute the position of foreign materials transverse of the sheet 2 on the basis of an output signal from the image sensor 7 for thereby moving the television camera 8 and the marker 9 transversely of the sheet 2. Additionally, the controller unit 10 has other functions of synchronizing the speed of withdrawal of the sheet 2 by the rollers 3, 4 and 5 with the speed of extrusion by the extruder 1, and of controlling power supply to the image sensor 7. The controller unit 10 may comprise a microcomputer which is commercially available.

The image analyzer 11 analyzes the image of foreign matter picked up by the television camera 8 to compute the total number and area of foreign materials, the average area of one foreign material, the number of those foreign materials which have maximum horizontal lengths exceeding a predetermined size, or the oversize count, the particle size distribution, and other statistical values. The image analyzer 11 may comprise an image analyzer LUZEX 450 manufactured by Nihon Regulator Co., Ltd. as combined with an optional classifier 9815A manufactured by Nihon Regulator Co., Ltd.

Figure 3A:
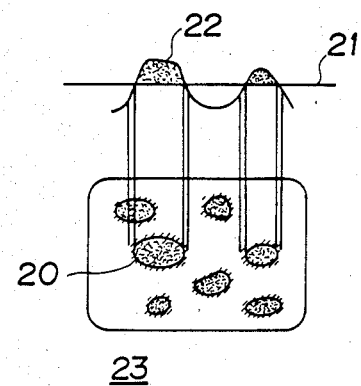
FIG. 3(a) is a diagram illustrative of the manner in which an image is binarized by a threshold circuit in an image analyzer.
Figure 3B:
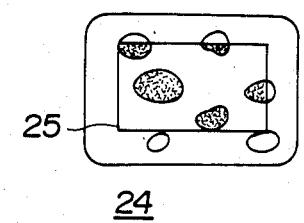
FIG. 3(b) is a diagram showing the manner in which a zone of measurement of a binarized image is determined by a framing circuit.

To determine the density and level of measurement, the image analyzer LUZEX 450 has a shading correction circuit for correcting ununiform brightnesses of an image due to sensitivity irregularities of the television camera 8. The shading correction circuit is supplied with an image signal for effecting parabollic shading correction and sawtooth-waveform shading correction for horizontal and vertical adjustment, thereby producing a corrected image having even brightness. The image analyzer also has a threshold circuit 23, as shown in FIG. 3(a), for sampling an optical density region 20 of a particle being measured as a region 21 on a line 21 to thereby convert the image into a binarized image which only has black and white areas without intermediate density regions. The binarized image is then supplied to a framing circuit 24, as shown in FIG. 3(b), for determining a field or zone of measurement. The framing circuit 24 cuts off a portion of the image to select those particles which are positioned within a frame 25 that determines the zone of measurement. The zone of measurement is moved around to define a number of zones of measurement which are not overlapped. The framed images are supplied to a counter circuit (not shown) dependent on measurement modes as set to compute the number of particles present in each zone, the total areas of the particles, the average area of the particles, the ratio of the total particle areas to the area of the zone of measurement, the oversize count or the number of those particles which have maximum horizontal lengths exceeding a predetermined size, the particle size distribution with respect to the predetermined size, and other data. These data are computed within one to two seconds for each field of view. The image analyzer also has a function of converting average-size particles to particles of actual sizes and reproducing them as an image. The classifier 9815A serves to cumulate the above measured data in all of the fields or zones of measurement for thereby computing secondary data.

Since the sheet 2 does not includes a large number of foreign materials and the television camera 8 has a small field of view of an increased accuracy, it is unlikely to have a plurality of foreign materials which enter the field of view of the television camera 8. However, cumulative processing in the image analyzer 11 can produce various statistical values of foreign materials, such as the total number of foreign materials included in the sheet 2 being inspected, their total areas, their average area, and other data. These statistical values are supplied via the controller unit 10 to the printer 14 so as to be printed on a sheet, and at the same time to the display unit 15 for enabling the operator to visually check the displayed data and make necessary judgements. The statistical values are also fed to the videotape recorder 13 for recording. The videotape recorder 13 also records the image of an average foreign material that is reproduced to actual size. This image can also be displayed on the monitor television picture tube 12.

With the automatic inspection system according to the present invention, the kind and the position of foreign materials included in a sheet of resin compound is detected by an image sensor to move a television camera for enabling the latter to pick up the image of the foreign materials and to supply the image to an image analyzer in which the image is analyzed. Therefore, the sizes, the kinds, number and other date of the detected foreign materials can be measured to a nicety within a short period of time for immediate determination of the acceptability and grade of the resin material being inspected. Although conventional visual inspection takes 45 minutes to inspect a sample sheet that is 1 m long and can detect foreign materials having a size of 40 microns and larger, the automatic inspection system of the invention is capable of inspecting 1 m of sheet in little less than one and half minutes and of detecting particles having a size on the order to 25 microns.

Thus, there is provided in accordance with the invention an automatic inspection system for detecting foreign matter which has the advantages discussed above. The embodiment described is intended to be merely exemplary and those skilled in the arm will be able to make variations and modifications in them without departing from the spirit and scope of the invention. All such modifications and variations are contemplated as falling within the scope of the claims.

What is claimed is:

1. An automatic inspection system for detecting foreign materials in a resin material sheet, comprising:
    an extruder for extruding a resin material into a soft sheet capable of passing light therethrough;
    a source of light disposed on one side of said path of travel of said sheet; and
    an image sensor camera disposed on the other side of said path of travel of said sheet in confronting relation to said source of light for receiving light emitted from said source of light and having passed through said sheet to detect foreign material included in said sheet;
    a pair of freely rotatable rollers disposed between said extruder and said image sensor camera for permitting said sheet to hang down by gravity into a U-shape of a length sufficient to cool and harden said soft sheet, portions of said sheet while hanging down by gravity in a U-shape being substantially perpendicular to said path of travel of said sheet;
    sensor means for detecting a vertical position of said U-shaped portion of said sheet, said sensor means including only two sensors spaced apart in a vertical direction at a distance so that said sheet is not detected by either sensor when said sheet hangs down to a positon between said sensors;
    means for withdrawing said sheet along a path of travel;
    controller means for adjusting the speed of sheet withdrawal for said withdrawing means in response to the output signal for said sensor means, said controller means comprising a main synchronous control system for maintaining the speed of the withdrawal of said sheet by the withdrawing means in synchronization with the rate of extrusion by the extruder, said main synchronous control system including a rotary encoder for detecting the rate of extrusion, the output of said encoder being fed to a digital-to-analog converter that produces an analog signal that is processed and fed to an analog-to-digital converter, the output of the analog-to-digital converter being applied to a pulse amplifier which feeds an amplified signal to a pulse motor for driving said means for withdrawing said sheet, said controller means also comprising a corrective control system for compensating a speed difference between the extrusion rate and the withdrawal speed in response to the output signal from said sensor means, said corrective control system including a voltage to frequency converter for receiving said output signal from said sensor means, the output of said voltage to frequency converter being applied to said pulse amplifier.

2. An inspection system according to claim 1, further comprising a marker disposed downstream of a television camera positioned downstream of said image sensor camera with respect to said path of travel of said sheet, said marker marking an area of said sheet in which said foreign materials are present.

3. An inspection system according to claim 2, further comprising
    means for producing signals representing physical characteristics of foreign material imaged by said television camera, and
    a printer for printing results of analysis of the foreign material obtained by processing signals detected in said camera.

* * * * *